(12) United States Patent
Gatto

(10) Patent No.: US 7,112,558 B2
(45) Date of Patent: *Sep. 26, 2006

(54) LUBRICANT COMPOSITION CONTAINING PHOSPHOROUS, MOLYBDENUM, AND HYDROXY-SUBSTITUTED DITHIOCARBAMATES

(75) Inventor: Vincent J. Gatto, Midlothian, VA (US)

(73) Assignee: Afton Chemical Intangibles LLC, Richmond, VA (US)

( * ) Notice: Subject to any disclaimer, the term of this patent is extended or adjusted under 35 U.S.C. 154(b) by 92 days.

This patent is subject to a terminal disclaimer.

(21) Appl. No.: 10/067,978

(22) Filed: Feb. 8, 2002

(65) Prior Publication Data

US 2003/0211951 A1 Nov. 13, 2003

(51) Int. Cl.
*C10M 135/18* (2006.01)
*C10M 141/12* (2006.01)
*C07C 333/00* (2006.01)

(52) U.S. Cl. .................. 508/363; 508/364; 508/365; 508/371; 508/376; 508/438; 508/442; 508/444; 558/232; 558/236; 558/239

(58) Field of Classification Search ............... 508/364, 508/363
See application file for complete search history.

(56) References Cited

U.S. PATENT DOCUMENTS

| | | | |
|---|---|---|---|
| 3,356,702 A | 12/1967 | Farmer | |
| 3,407,222 A | 10/1968 | Lies | |
| 3,509,051 A | 4/1970 | Farmer | |
| 3,578,690 A | 5/1971 | Becker | |
| 3,867,359 A | 2/1975 | Beadle | |
| 4,098,705 A | 7/1978 | Sakurai | |
| 4,226,732 A | 10/1980 | Reinhard et al. | |
| 4,360,438 A | 11/1982 | Rowan | |
| 4,765,918 A | 8/1988 | Love | |
| 4,846,983 A | 7/1989 | Ward, Jr. | |
| 4,889,647 A | 12/1989 | Rowan | |
| 5,126,063 A | 6/1992 | Cardis et al. | |
| 5,137,647 A | 8/1992 | Karol | |
| 5,370,806 A | 12/1994 | Cardis et al. | |
| 5,650,381 A | 7/1997 | Gatto | |
| 5,665,684 A | 9/1997 | Arai | |
| 5,672,727 A | 9/1997 | Chiu | |
| 5,698,498 A | 12/1997 | Luciana et al. | |
| 5,736,491 A * | 4/1998 | Patel et al. ................ | 508/365 |
| 5,786,307 A | 7/1998 | Igarashi | |
| 5,807,813 A | 9/1998 | Yamada | |
| 5,814,587 A | 9/1998 | Vrahopoulou | |
| 5,837,657 A | 11/1998 | Fang | |
| 5,840,672 A | 11/1998 | Gatto | |
| 5,880,073 A | 3/1999 | Tomizawa | |
| 5,888,945 A | 3/1999 | Stiefel | |
| 5,895,779 A | 4/1999 | Boffa | |
| 5,916,851 A | 6/1999 | Hosonuma | |
| 5,925,600 A | 7/1999 | Atherton | |
| 6,017,858 A | 1/2000 | Karol | |
| 6,174,842 B1 | 1/2001 | Gatto | |
| 6,187,723 B1 * | 2/2001 | Holt et al. ................. | 508/364 |
| 6,329,328 B1 * | 12/2001 | Koganei et al. ............ | 508/365 |

FOREIGN PATENT DOCUMENTS

| | | |
|---|---|---|
| EP | 0874040 A1 | 10/1998 |
| EP | 1 306 370 A1 | 5/2003 |
| JP | 54-22414 | 2/1979 |
| JP | 9-111271 | 4/1997 |
| JP | 9-111274 | 4/1997 |
| JP | 10-88168 | 4/1998 |
| WO | WO96/37585 A1 | 11/1996 |
| WO | WO 00/55284 A1 | 9/2000 |

OTHER PUBLICATIONS

Belov et al., Chemical Abstracts 98:142922, Synthesis and properties of nitrogen-, sulfur-, and phosphorus-containing additives made from glycerol monochlorohydrin ethers, 1983.*

Latyuk et al., Database CAPLUS, Chemical Abstracts Service, (Columbus, Ohio), Acession No. 137:127291, "1-Alkylthiopropanol-2-derivatives as multifunctional additives to lubricating oils," abstract, NEFTEKHIMIYA, 2002, pp. 145-149, vol. 42, issue No. 2, (9 pages total).

* cited by examiner

*Primary Examiner*—Ellen M. McAvoy
(74) *Attorney, Agent, or Firm*—Paige J. Thomson; Dennis H. Rainear

(57) ABSTRACT

The invention relates to a lubricating composition comprising a base oil of lubricating viscosity, a hydroxy-substituted dithiocarbamate, an organo-molybdenum compound, and optionally a phosphorous source.

40 Claims, No Drawings
LUBRICANT COMPOSITION CONTAINING PHOSPHOROUS, MOLYBDENUM, AND HYDROXY-SUBSTITUTED DITHIOCARBAMATES

FIELD OF THE INVENTION

The present invention relates to lubricant compositions containing phosphorous, molybdenum, and hydroxy-substituted dithiocarbamates. New lubricant compositions are prepared by combining in a lubricating oil, (A) hydroxy-substituted dithiocarbamates, (B) organo-molybdenum compounds, and optionally, (C) a phosphorus compound, preferably zinc dialkyldithiophosphate (ZDDP). Lubricants prepared with compositions of the present invention are effective as wear inhibitors when used in passenger car engine oils.

BACKGROUND OF THE INVENTION

Dithiocarbamates have been known for some time. Examples of various structurally different dithiocarbamates are disclosed in the following patents:

| | | | | |
|---|---|---|---|---|
| 3,407,222 | 5,693,598 | 4,885,365 | 4,125,479 | 5,902,776 |
| 3,867,359 | 5,686,397 | 4,836,942 | 4,758,362 | 3,509,051 |
| 2,710,872 | 5,789,357 | 4,927,552 | 5,629,272 | 3,356,702 |
| 5,840,664 | 4,957,643 | 4,876,375 | 5,759,965 | 4,098,705 |

Examples of hydroxy-substituted dithiocarbamates are disclosed in the following references and patents: Zh. Org. Khim. (1991), 27(1), 161–170; Zh. Org. Khim. (1988), 24(2), 286–291; Z. Chem. (1987), 27(1), 24–25; Zh. Org. Khim. (1985), 21(6), 1173–1176: Neftekhim (1983), 23(3), 409–412; Neftepererab. Neftekhim. (Moscow) (1983), (1), 20–22; U.S. Pat. No. 3,407,222; and U.S. Pat. No. 3,867,359.

Examples of commercially available dithiocarbamates include Vanlube(R)® 7723, a methylenebis(dibutyldithiocarbamate), Molyvan® A, a molybdenum oxysulfide dithiocarbamate, Molyvan® 822, an organo molybdenum dithiocarbamate, Vanlube® AZ, a zinc diamyldithiocarbamate, Vanlube® 71, a lead diamyldithiocarbamate, Vanlube® 73, an antimony dialkyldithiocarbamate, and Vanlube® 732, a dithiocarbamate derivative, all obtained from R. T. Vanderbilt Company, Inc.

There are many examples in the patent literature showing the use of molybdenum additives as antioxidants, deposit control additives, anti-wear additives and friction modifiers, including:

| | | | |
|---|---|---|---|
| U.S. Pat. No. 5,840,672 | U.S. Pat. No. 5,814,587 | U.S. Pat. No. 4,529,526 | WO 95/07966 |
| U.S. Pat. No. 5,650,381 | U.S. Pat. No. 4,812,246 | U.S. Pat. No. 5,458,807 | WO 95/07964 |
| U.S. Pat. No. 5,880,073 | U.S. Pat. No. 5,658,862 | U.S. Pat. No. 5,696,065 | WO 95/07963 |
| U.S. Pat. No. 5,665,684 | U.S. Pat. No. 4,360,438 | U.S. Pat. No. 5,736,491 | WO 95/27022 |
| U.S. Pat. No. 5,786,307 | U.S. Pat. No. 4,501,678 | U.S. Pat. No. 5,688,748 | EP 0 447 916 A1 |
| U.S. Pat. No. 5,807,813 | U.S. Pat. No. 4,692,256 | U.S. Pat. No. 5,605,880 | WO 95/07962 |
| U.S. Pat. No. 5,837,657 | U.S. Pat. No. 4,832,867 | U.S. Pat. No. 4,705,641 | EP 0 768 366 A1 |
| U.S. Pat. No. 5,925,600 | U.S. Pat. No. 5,922,654 | U.S. Pat. No. 5,916,851 | U.S. Pat. No. 5,895,779 |
| U.S. Pat. No. 5,888,945 | U.S. Pat. No. 5,939,364 | U.S. Pat. No. 6,074,993 | U.S. Pat. No. 6,063,741 |
| U.S. Pat. No. 6,017,858 | U.S. Pat. No. 5,994,277 | U.S. Pat. No. 5,824,627 | U.S. Pat. No. 5,763,374 |
| U.S. Pat. No. 4,995,996 | U.S. Pat. No. 4,990,271 | U.S. Pat. No. 4,978,464 | U.S. Pat. No. 4,846,983 |
| U.S. Pat. No. 4,832,857 | U.S. Pat. No. 4,478,729 | U.S. Pat. No. 4,466,901 | U.S. Pat. No. 4,428,848 |
| U.S. Pat. No. 4,414,122 | U.S. Pat. No. 4,402,840 | U.S. Pat. No. 4,395,343 | U.S. Pat. No. 4,394,279 |
| U.S. Pat. No. 4,369,119 | U.S. Pat. No. 4,362,633 | U.S. Pat. No. 4,357,149 | U.S. Pat. No. 4,324,672 |
| U.S. Pat. No. 4,285,822 | U.S. Pat. No. 4,283,295 | U.S. Pat. No. 4,272,387 | U.S. Pat. No. 4,265,773 |
| U.S. Pat. No. 4,263,152 | U.S. Pat. No. 4,261,843 | U.S. Pat. No. 4,259,195 | U.S. Pat. No. 4,259,194 |
| U.S. Pat. No. 4,248,720 | U.S. Pat. No. 4,202,781 | U.S. Pat. No. 4,201,683 | U.S. Pat. No. 4,192,757 |
| U.S. Pat. No. 4,178,258 | U.S. Pat. No. 4,164,473 | U.S. Pat. No. 4,098,705 | U.S. Pat. No. 3,733,345 |
| EP 0 874 040 A1 | EP 0 822 246 A3 | EP 0 768 366 A1 | WO 00/08120 |
| WO 95/07963 A1 | WO 95/07964 A1 | WO 95/07965 A1 | WO 95/07966 A1 |
| WO 95/27022 A1 | WO 96/19551 A1 | | |

Examples showing the use of a combination of molybdenum and other ashless dithiocarbamates are found in U.S. Pat. No. 4,360,438; U.S. Pat. No. 6,017,858; WO 96/37585, and EP 0874040 A1.

Studies have suggested that emissions systems can be deactivated as a result of contamination from compounds derived from the engine oil. Other studies have suggested that emissions system durability may be improved by using lubricants containing high metal/phosphorus ratios. Reducing the level of phosphorus in the engine oils has also been suggested as a means of prolonging the efficiency of the catalytic converter. The phosphorus in engine oils originates primarily from zinc dithiophosphates (ZDDP's), which are used to prevent wear and control oxidation. Over the years ZDDP's have demonstrated reliable anti-wear and antioxidant effectiveness. Most engine builders would not recommend engine oils which contain substantial reductions from today's ZDDP levels without extensive proof in the laboratory and the field that wear protection is acceptable. Commercial engine oils meeting API SJ requirements usually contain approximately 0.10 wt. % phosphorus derived from ZDDP. A substantial reduction in ZDDP's, which may be required for catalytic converter durability, would result in significantly higher engine wear and oil oxidation. To compensate for the use of less ZDDP in engine oils, supplemental wear and oxidation inhibitors are required.

SUMMARY OF THE INVENTION

The lubricant compositions described in an embodiment of this invention act to improve wear and oxidation performance in engine oils containing reduced levels of ZDDP's, i.e. engine oils containing reduced levels of phosphorus.

The present invention provides in an embodiment a lubricant composition comprising an oil of lubricating viscosity, a molybdenum source, a hydroxy-substituted dithiocarbamate, and optionally, a phosphorous source.

A benefit the compositions of an embodiment of the present invention is to provide reduced friction in fully formulated crankcase oils containing low levels of ZDDP's.

One advantage of the two-component additive system of the present invention comprised of hydroxy-substituted dithiocarbamates and a molybdenum compound is that the combination can be used to develop zero phosphorus crankcase oils.

A principle advantage of the three-component additive system of the present invention comprised of hydroxy-substituted dithiocarbamates, a molybdenum compound, and a phosphorus compound in a base oil is that the combination can be used to develop low phosphorus crankcase oils. One advantage of such oils is reduced poisoning of the automotive catalyst caused by phosphorus contamination of the fuel which over the extended life of an automobile or truck translates to reduced emissions and reduced pollution.

An additional advantage of the use of hydroxy-substituted dithiocarbamates in lubricating oil for automotive crankcase is their reduced thermal stability, as determined by Thermal Gravimetric Analysis (TGA), which manifests itself, when used in combination with molybdenum and phosphorus as claimed herein, in improved low temperature wear protection. A further advantage of the use of hydroxy-substituted dithiocarbamates in lubricating oil for automotive crankcase is that they are hydrolytically stable.

This invention describes in an embodiment a new class of crankcase lubricants prepared by combining, in a lubricating oil, (A) hydroxy-substituted dithiocarbamate(s), (B) organo-molybdenum compounds, and optionally, (C) a phosphorus compound, preferably zinc dialkyldithiophosphate (ZDDP). These new compositions may be used in a wide variety of crankcase oils including passenger car engine oils, heavy-duty diesel engine oils, railroad oils, and natural gas engine oils. The compositions of the present invention can be used to deliver wear and oxidation protection in a wide variety of lubricant types. The compositions can also be used in combination with other wear inhibitors, such as friction modifiers, to provide additional wear protection when required. In this case, the compositions of the present invention would be considered the principle wear-inhibiting component of the total wear inhibitor system. Used as such they can be applied towards the development of low phosphorus (in the presence of component C) or zero phosphorus (in the absence of component C) crankcase oils.

As mentioned above, the new lubricant compositions are prepared in an embodiment of the present invention by combining, in a lubricating oil, (A) one or more hydroxy-substituted dithiocarbamates, (B) one or more organo-molybdenum compounds, and optionally, (C) one or more phosphorus compounds, preferably zinc dialkyldithiophosphate (ZDDP).

When components A and B are present in the absence of C, the lubricating compositions of the present invention can be used to produce phosphorus-free crankcase oils. When components A, B, and C are present, phosphorus-containing crankcase oils can be produced.

It is to be understood that both the foregoing general description and the following detailed description are exemplary and explanatory only and are intended to provide further explanation of the present invention, as claimed.

DETAILED DESCRIPTION OF THE PRESENT INVENTION

A description of the individual components of the new lubricant compositions is provided below.

A. The Hydroxy-Substituted Dithiocarbamates

The chemical structure of the hydroxy-substituted dithiocarbamates is shown below where R and R' may be hydrogen or alkyl with the requirement that at least one of R or R' is alkyl, R" is hydrogen, alkyl, R'''XCH$_2$, R'''O(C=O)CH$_2$XCH$_2$, or R'''O(C=O)CH$_2$CH$_2$XCH$_2$ where R''' is alkyl, and X is oxygen (O) or sulfur (S).

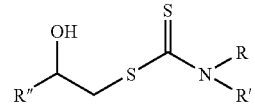

It is desirable that the total sum of carbons in R, R' and R" be greater than eight so that the additive is of low volatility and remains in the formulated crankcase oil at elevated operating temperatures. Additives with eight or less carbons are too volatile for use in the high temperature crankcase environment. In use, such volatile components would evaporate out of the crankcase before they could perform their anti-wear and anti-oxidant functions. Typical alkyl groups for R, R', R", and R''' may vary from 1 to 22 carbons and include all possible linear, or n-, and branched, or iso-, alkyl isomers. Examples of typical alkyl groups include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, and octadecyl and include all possible isomers of each alkyl type. For example, the 2-ethylhexyl alkyl group [—CH$_2$CH(CH$_2$CH$_3$)CH$_2$CH$_2$CH$_2$CH$_3$] is considered an isomer of the n-octyl group [—CH$_2$CH$_2$CH$_2$CH$_2$CH$_2$CH$_2$CH$_2$CH$_3$].

These hydroxy-substituted dithiocarbamates may be prepared, in one embodiment, by combining at approximately equal molar concentrations an epoxide, a primary or secondary amine, and carbon disulfide. The reactions are generally carried out at low temperatures.

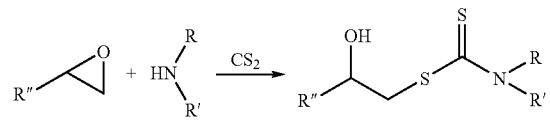

It is preferred that equal molar concentrations of the three components be used. However, a small excess of any one or two components may be used, especially if the excess can be removed once the reaction is complete. For example, a typical molar ratio of epoxide to amine to carbon disulfide may be 1:1:1.2 where a slight excess of carbon disulfide is used. Alternatively a ratio of 1.2:1:1.2 may be used in which case a slight excess of epoxide and carbon disulfide is used. When excess reagents are used it is preferred that they be volatile so that they can be removed by distillation or vacuum distillation, after the desired product is produced.

Examples of epoxides that may be used include ethylene oxide, propylene oxide, 1,2-butylene oxide, 1,2-epoxypentane, 1,2-epoxyhexane, 1,2-epoxyheptane, 1,2-epoxyoctane, 1,2-epoxynonane, 1,2-epoxydecane, 1,2-epoxyundecane, 1,2-epoxydodecane, 1,2-epoxytridecane, 1,2-epoxytetradecane, 1,2-epoxypentadecane, 1,2-epoxyhexadecane, 1,2-epoxyheptadecane, 1,2-epoxyoctadecane, methyl glycidyl ether, ethyl glycidyl ether, propyl glycidyl ether, butyl glycidyl ether, pentyl glycidyl ether, hexyl glycidyl ether, cyclohexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, heptadecyl glycidyl ether, octadecyl glycidyl ether, methyl glycidyl thioether, ethyl glycidyl thioether, propyl glycidyl thioether, butyl glycidyl thioether, pentyl glycidyl thioether, hexyl glycidyl thioether, cyclohexyl glycidyl thioether, heptyl glycidyl thioether, octyl glycidyl thioether, nonyl glycidyl thioether, decyl glycidyl thioether, undecyl glycidyl thioether, dodecyl glycidyl thioether, tridecyl glycidyl thioether, tetradecyl glycidyl thioether, pentadecyl glycidyl thioether, hexadecyl glycidyl thioether, heptadecyl glycidyl thioether, octadecyl glycidyl thioether. Also useful herein as the epoxide is styrene oxide. In addition, all possible isomers of these epoxides may be used and mixtures of these epoxides may be used. Additional epoxides that may be used include:

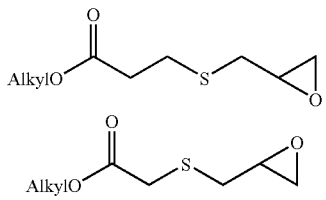

where the alkyl group can vary from methyl to octadecyl and include all possible linear, or n-, and branched, or -iso, alkyl isomers.

Methods of producing alkylglycidyl thioethers are reported in U.S. Pat. Nos. 4,931,576 and 5,618,778.

Examples of amines that may be used include methylamine, dimethylamine, ethylamine, diethylamine, butylamine, dibutylamine, pentylamine, dipentylamine, hexylamine, dihexylamine, heptylamine, diheptylamine, octylamine, dioctylamine, nonylamine, dinonylamine, decylamine, didecylamine, undecylamine, bis(undecyl)amine, dodecylamine, bis(dodecyl)amine, tridecylamine, bis(tridecyl)amine, tetradecylamine, bis(tetradecyl)amine, pentadecylamine, bis(pentadecyl)amine, hexadecylamine, bis(hexadecyl)amine, heptadecylamine, bis(heptadecyl)amine, octadecylamine, bis(octadecyl)amine. In addition, all possible isomers of these amines may be used and mixtures of these amines may be used. In addition, secondary amines containing different alkyl groups may be used. For example, an amine such as butyloctylamine may be used.

A diluent may be used in the reaction but such diluents are not necessary. In fact, it is preferred that a diluent not be used in order to keep manufacturing costs low and production cycle times short. Examples of diluents include water, alcohols, hydrocarbon solvents, aromatic solvents, chlorinated solvents, polar aprotic solvents, diluent oils, process oils, and base oils. Diluents may be carried over from the preparation of the epoxides and used in the subsequent preparation of the hydroxy-substituted dithiocarbamates. For example, hydroxy dithiocarbamates may be prepared in two steps by first preparing the epoxide from a mercaptan and epichlorohydrin, followed by reaction of the epoxide with the amine and carbon disulfide. In such a case the water from the preparation of the epoxide is carried over into the reaction to prepare the hydroxy-substituted dithiocarbamates. This allows the preparation of hydroxy-substituted dithiocarbamates from readily available raw materials in two reaction steps using only one reactor.

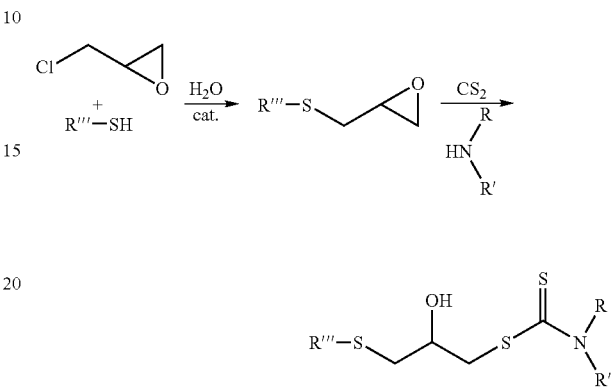

A catalyst may be used in the reaction, but such catalysts are not necessary. In fact, it is preferred that a catalyst not be used in order to keep manufacturing costs low and production cycle times short. However, catalysts may be required to improve yields of the hydroxy-substituted dithiocarbamates. Examples of catalysts that may be used include the alkali and alkaline earth metal hydroxides such as lithium hydroxide, sodium hydroxide, potassium hydroxide, magnesium hydroxide, and calcium hydroxide. The catalyst may be used as a true catalyst, where the concentration is less than stoichiometric relative to the amine, or it may be used as a reagent, where the concentration is stoichiometric or greater relative to the amine.

The reaction between amines, carbon disulfide, and epoxides are exothermic and as such do not require heating. In fact, the combination of the three components will generate substantial heat and usually requires cooling for control and to prevent loss of the volatile carbon disulfide. Reaction temperatures can vary from 0° C. to 30° C. during the combination of the components, and from 20° C. to 80° C. after the component addition.

A typical reaction involves adding, over 1 hour, the amine to a stirred solution containing carbon disulfide and epoxide at a temperature controlled between 0 and 15° C. by the addition rate. After the addition the reaction mixture is heated at 60 to 80° C. for 1 to 2 hours. A vacuum strip may be used to remove excess or residual carbon disulfide, epoxide, or unreacted amine. The vacuum strip is generally performed for 1 to 2 hours at 60 to 80° C. Solvents, if used, may be removed by distillation or vacuum distillation. Catalysts, if used, may be removed by carrying out a series of aqueous washes and/or filtrations. Again, it is preferred to carry out these reactions in the absence of solvent and catalysts. Modifications to the reactions may be made without substantially changing the product produced. For example, trace quantities of hydrogen peroxide may be added to reduce the odor of certain products.

When the hydroxy-substituted dithiocarbamates are prepared in two steps from the mercaptan or alcohol, it is possible that small quantities of by-products may form. For example, unreacted epichlorohydrin in the first step may react with two equivalence of amine and two equivalence of carbon disulfide to form a product of the type shown below where R

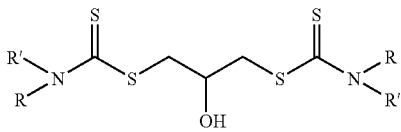

and R' are as defined above.

The presence of this compound in small quantities in the product is not detrimental and may in fact be beneficial since it possesses structural features similar to the hydroxy-substituted dithiocarbamates. The presence of this compound can be eliminated by purification of the intermediate epoxide.

A small amount of epichlorohydrin in the first step may react with two equivalence of mercaptan or alcohol to form a product of the type shown below where W''' is as defined above and

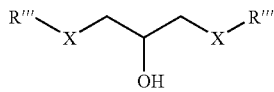

X=O (for alcohol reactants) or S (for mercaptan reactants). The presence of this compound in small quantities in the product is not detrimental and may in fact be beneficial since it possesses structural features similar to the alkylthio and hydroxy-substituted dithiocarbamates. The presence of this compound can be eliminated by purification of the intermediate epoxide.

The amount of hydroxy-substituted dithiocarbamate added to the finished crankcase oil will vary depending upon the customers' requirements and the specific application. Typical treat levels may vary from 0.05 wt. % to 1.5 wt. % and are generally dependent upon the performance requirements of the finished oil and the amount of sulfur present in the hydroxy-substituted dithiocarbamate. Treat levels for these types of additives may also be expressed as the amount of sulfur being delivered to the finished crankcase oil. Expressed in this way, typical treat levels may vary from 100 ppm delivered sulfur (0.01 wt. %) to 3000 ppm (0.3 wt. %) delivered sulfur.

B. Molybdenum Compounds

Molybdenum compounds derived from carboxylic acids, carboxylic acid amides, or fatty acid amides are described in U.S. Pat. No. 6,174,842; U.S. Pat. No. 3,578,690; U.S. Pat. No. 4,765,918; U.S. Pat. No. 4,889,647; and U.S. Pat. No. 5,137,647.

Examples of commercial molybdenum carboxylate compounds derived from carboxylic acids that may be used in the present invention include, for example and without limitation herein, 15% Molybdenum HEX-CEM, available from OM Group, Inc., Molybdenyl Naphthenate 6% and Molybdenum Octoate 8%, available from the Shepherd Chemical Company.

Examples of commercial molybdenum compounds derived from organic amides that may be used include Molyvan® 855 and Molyvan® 856B, available from the R. T. Vanderbilt Company, Inc., and HiTEC® 4716 available from Ethyl Petroleum Additives, Inc.

Molybdenum dialkyldithiocarbamates are described in U.S. Pat. Nos. 4,098,705; 4,846,983; 5,916,851; 3,356,702; 3,509,051; and 4,098,705.

Examples of commercial molybdenum dialkyldithiocarbamates that may be used in the present invention include Molyvan® 807 and Molyvan® 822, available from the R. T. Vanderbilt Company, Inc., and Sakura-Lube 100, Sakura-Lube 155, Sakura-Lube 165 and Sakura-Lube 600, available from Asahi Denka Kogyo K. K.

The amount of molybdenum added to the lubricating oil to produce the finished crankcase oil will vary depending upon the customers' requirements and the specific application. Typical treat levels may vary from 0.02 wt. % to 3.0 wt. % and are generally dependent upon the performance requirements of the finished oil and the amount of molybdenum present in the organo-molybdenum compound. Treat levels for these types of additives may also be expressed as the amount of molybdenum being delivered to the finished crankcase oil. Expressed in this way, typical treat levels may vary from 25 ppm delivered molybdenum (0.0025 wt. %) to 1500 ppm (0.15 wt. %) delivered molybdenum. The molybdenum source can be selected in an embodiment from the group consisting of molybdenum carboxylates, molybdenum complexes of organic amides, molybdenum complexes of organic amines, and molybdenum dialkyldithiocarbamates.

C. Phosphorus Compounds

The presence of phosphorus compounds is optional. The preferred phosphorus compound, if present, is zinc dialkyldithiophosphate (ZDDP). Treat levels for ZDDP in API SJ passenger car engine oils are expressed as the amount of phosphorus delivered to the oil and are typically 1000 ppm phosphorus (0.1 wt. % phosphorus). The ZDDP may be primary or secondary or mixed primary/secondary. The ZDDP may also be a neutral ZDDP or an overbased ZDDP. Examples of commercial ZDDP's that may be used include HiTEC® 7169, a secondary ZDDP, HiTEC® 7197, HiTEC® 680 and HiTEC® 682, all primary ZDDP's, and HiTEC® 1656, a mixed primary/secondary ZDDP, all available from Ethyl Corporation.

Low phosphorus crankcase oils may be prepared using the three-component additive combination of the present invention by using lower treat levels of the phosphorus compound. For example, a passenger car engine oil containing about 500 ppm phosphorus may be prepared using the following combination of additives:

0.6 wt. % ZDDP (HiTEC® 7169 from Ethyl Corporation) to deliver 500 ppm phosphorus to the finished passenger car engine oil;

0.4 wt. % organo-molybdenum compound (Molyvan® 855 from the R. T. Vanderbilt Company) to deliver 320 ppm molybdenum to the finished passenger car engine oil; and 0.5 wt. % of a hydroxy-substituted dithiocarbamate containing 20 wt. % sulfur to deliver 1000 ppm sulfur to the finished passenger car engine oil;

Zero phosphorus crankcase oils may be prepared by eliminating the phosphorus. For example, a passenger car engine oil containing zero phosphorus may be prepared using the following combination of additives:

0.4 wt. % organo-molybdenum compound (Molyvan® 855 from the R. T. Vanderbilt Company) to deliver 320 ppm molybdenum to the finished passenger car engine oil;

0.5 wt. % of a hydroxy-substituted dithiocarbamate containing 20 wt. % sulfur to deliver 1000 ppm sulfur to the finished passenger car engine oil; and 0.5 wt. % of a supplemental organic friction modifier.

Any phosphorus compound that has antioxidant activity may be used. Examples of additional phosphorus compounds that may be used include alkyl phosphites, aryl phosphites, mixed alkyl/aryl phosphites, alkyl thiophosphites, aryl thiophosphites, mixed alkyl/aryl thiophosphites, alkyl phosphates, aryl phosphates, mixed alkyl/aryl phosphates, metal or amine salts of phosphorodithioic acids, ashless dialkyldithiophosphates, ashless diaryldithiophosphates, and mixed ashless alkyl/aryldithiophosphates. A preferred phosphorus source contains zinc diethyl/diisopropyl dithiophosphate.

The three component additive system described in this invention produces crankcase lubricants with improved wear performance that can be utilized to develop crankcase oils containing conventional levels of phosphorus (approximately 1000 ppm P), low phosphorus oils (approximately 500 ppm P to less than 1000 ppm P) or zero phosphorus oils. Examples of typical applications include passenger car engine oils, heavy-duty diesel engine oils, railroad oils, and natural gas engine oils.

The lubricating compositions of the present invention can be blended in base oils of a lubricating viscosity. The base oil of lubricating viscosity can be selected from animal oils, vegetable oils, mineral lubricating oils, solvent or acid treated mineral oils, oils derived from coal or shale, hydrocarbon oils, halo-substituted hydrocarbon oils, alkylene oxide polymers, esters of dicarboxylic acids, esters of polyols, esters of phosphorus-containing acids, polymeric tetrahydrofurans, silicon-based oils, and mixtures thereof.

EXAMPLES

Examples below demonstrate the preparation of the hydroxy-substituted dithiocarbamates and molybdenum compounds. Properties such as anti-wear performance are also demonstrated. Proper use of the hydroxy-substituted dithiocarbamate/molybdenum in combinations with zinc dialkyldithiophosphates can according to the present invention enable the commercial development of low phosphorus passenger car and heavy duty diesel engine oils.

Example 1

A 250 mL four neck round bottom flask is equipped with a magnetic stirrer, an addition funnel, a thermometer, and a nitrogen inlet. A slight positive pressure of nitrogen atmosphere is maintained in the reaction flask. The reactor is charged with 2-ethylhexyl glycidyl ether (28.0 g, 0.150 mol) and carbon disulfide (13.0 g, 0.171 mol). The mixture is stirred with cooling to approximately room temperature (tap water bath). Bis(2-ethylhexyl)amine (35.8 g, 0.148 mol) is slowly added to the reaction over a 1 hour period. An exotherm is observed and the addition is controlled to keep the reaction temperature under 30° C. After 4 hours at ambient temperature the mixture is gently heated for 1 hour at 50° C. The reaction mixture is cooled below 30° C. and an additional charge of carbon disulfide (1.2 g, 0.016 mol) is added. Stirring at ambient temperature is continued overnight. The next morning the reaction is heated to 50° C. and held at that temperature, under vacuum, for 1.5 hours. A yellow viscous liquid (74.7 g, 98.7%) is isolated. Sulfur content=12.41 wt % (theory=12.72 wt %), Nitrogen content=2.94 wt % (theory=2.78 wt %). Low molecular weight GPC analysis of the liquid shows the presence of a single peak (100%, r. t.=22.3 min). FT-IR, $^{13}$C-NMR and H-NMR analysis confirms that the main component of the mixture is 3-(2-ethylhexyloxy)-2-hydroxypropyl bis(2-ethylhexyl)carbamodithioate having the following chemical structure:

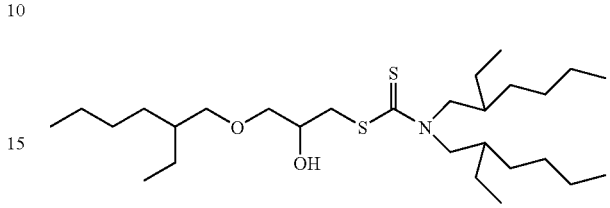

Example 2

A 250 mL four neck round bottom flask is equipped with a magnetic stirrer, an addition funnel, a thermometer, and a nitrogen inlet. A slight positive pressure of nitrogen atmosphere is maintained in the reaction flask. The reactor is charged with 2-ethylhexyl glycidyl ether (28.0 g, 0.150 m) and carbon disulfide (14.3 g, 0.188 m). The mixture is stirred with cooling to approximately room temperature (tap water bath). Dibutylamine (19.2 g, 0.149 m) is slowly added to the reaction over a 30 minute period. An exotherm is observed and the addition is controlled to keep the reaction temperature under 30° C. After 2 hours at ambient temperature the mixture is gently heated for 2 hours at 35° C. followed by 1 hour at 50° C. Volatiles are removed under vacuum at 50° C. for 1.5 hours. A yellow viscous liquid (57.8 g, 95.7%) is isolated. Sulfur content=16.07 wt % (theory=16.37 wt %), Nitrogen content=3.86 wt % (theory=3.58 wt %). Low molecular weight GPC analysis of the liquid shows the presence of predominantly one peak (99%, r. t.=23.0 min). FT-IR, $^{13}$C-NMR and H-NMR analysis confirms that the main component of the mixture is 3-(2-ethylhexyloxy)-2-hydroxypropyl dibutylcarbamodithioate having the following chemical structure:

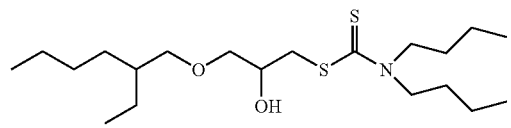

Examples 3–8

Using procedures analogous to that described in Example 1 and 2, the following additional hydroxy-substituted dithiocarbamates were prepared.

| Compound | Sulfur (wt %) | Nitrogen (wt %) | Low MW GPC (Area %) |
| --- | --- | --- | --- |
| Example 3 [structure: CH3-CH(OH)-CH2-S-C(=S)-N(nBu)2] | 23.8 | 5.51 | 99.2 |
| Example 4 [structure: CH3-CH(OH)-CH2-S-C(=S)-N(2-ethylhexyl)2] | 16.6 | 4.0 | 99.1 |
| Example 5 [structure: nC10H21-CH(OH)-CH2-S-C(=S)-N(nBu)2] | 15.2 | 3.6 | 98.9 |
| Example 6 [structure: nC16H33-CH(OH)-CH2-S-C(=S)-N(nBu)2] | 11.7 | 3.0 | 96.7 |
| Example 7 [structure: CH3(CH2)x-O-CH2-CH(OH)-CH2-S-C(=S)-N(nBu)2, x = 1-3] | 12.2 | 3.2 | 96.5 |
| Example 8 [structure: 2-ethylhexyl-O-CH2-CH(OH)-CH2-S-C(=S)-NH-CH2-(2-ethylhexyl)] | 15.9 | 3.7 | 97.2 |

Example 9

A 1000 mL four neck round bottom flask is equipped with a mechanical stirrer, an addition funnel, a thermometer, and a reflux condenser cooled to approximately 5° C. Dry nitrogen is passed into the reactor through the addition funnel and out of the reactor through the reflux condenser. The reactor is chilled with an ice water bath and charged with epichlorohydrin (46.3 g, 0.50 mol) and tert-dodecylmercaptan (101.1 g, 0.50 mol). The mixture is stirred with cooling to approximately 5–10° C. Sodium hydroxide (21.2 g, 0.53 mol), water (230 g) and tetrabutylammonium hydroxide (40% in water, 6.0 g, 6 mmol) are combined with mixing and slowly added to the epichlorohydrin and tert-dodecylmercaptan over a 1 hour period. An exotherm is observed and cooling is continued maintaining the reaction temperature between 5–10° C. during the addition. After the addition the reaction is heated for 2 hours at 50° C. and cooled to 5° C. Carbon disulfide (40.0 g, 0.53 mol) is then added rapidly to the reaction mixture. Next, dibutylamine (65.0 g, 0.50 mol) is slowly added over 1 hour while maintaining the reaction temperature between 5–15° C. The reaction is warmed to ambient temperature overnight. The following morning the reaction is heated at 80° C. for 1 hour and then 0.60 g of 30% hydrogen peroxide is added at 70° C. The reaction is heated at 70° C. for an additional 15 minutes, cooled to 50° C., and the phases separated. The organic portion is washed with 2×100 mL of water. The organic solution is returned to a 500 mL three neck round bottom flask and residual water is removed under vacuum at 60° C. for 3 hours. The product is filtered through a coarse fritted glass funnel yielding 220.0 g (94.5%) of a clear yellow viscous liquid with the following physical and chemical properties:

| | |
|---|---|
| Nitrogen Content | 3.14 wt % |
| Sulfur Content | 19.68 wt % |
| Viscosity @ 40° C. | 295 cSt |
| Low Molecular Weight GPC Analysis | 97.1% dialkylated product (r.t. = 22.7 min) |
| TGA Weight Loss | 10% loss @ 212° C. |
| | 25% loss @ 241° C. |
| | 50% loss @ 268° C. |

FT-IR, $^{13}$C-NMR and H-NMR analysis confirms that the main component of the mixture is the 3-(tert-dodecylthio)-2-hydroxypropyl dibutylcarbamodithioate having the following chemical structure.

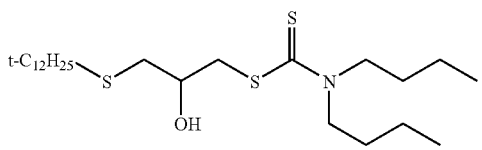

Example 10

A 2000 mL four neck round bottom flask is equipped with a mechanical stirrer, an addition funnel, a thermometer, and a reflux condenser cooled to approximately 5° C. Dry nitrogen is passed into the reactor through the addition funnel and out of the reactor through the reflux condenser. The reactor is chilled with an ice water bath and charged with epichlorohydrin (138.9 g, 1.50 mol) and 2-ethylhexyl 3-mercaptopropionate (327.6 g, 1.50 mol). The mixture is stirred with cooling to approximately 5–10° C. Sodium hydroxide (63.0 g, 1.58 mol), water (700 g) and tetrabutylammonium hydroxide (40% in water, 18.8 g, 19 mmol) are combined with mixing and slowly added to the epichlorohydrin and 2-ethylhexyl 3-mercaptopropionate over a 1 hour period. An exotherm is observed at the beginning of the addition that causes the temperature to reach 80° C. The temperature is returned to 5° C. and cooling is continued maintaining the reaction temperature between 5–10° C. for the remainder of the addition. After the addition the reaction is heated for 2 hours at 50° C. and cooled overnight. The following morning the reaction is cooled to 5° C. and carbon disulfide (120.0 g, 1.58 mol) is added.

Next, dibutylamine (193.8.0 g, 1.50 mol) is slowly added over 1 hour while maintaining the reaction temperature between 5–15° C. The reaction is heated at 80° C. for 1 hour and then 5.0 g of 30% hydrogen peroxide is added at 70° C. The reaction is heated at 70° C. for an additional 15 minutes, cooled to 50° C., and the phases separated. The organic portion is washed with 400 mL of 10% aqueous sodium bicarbonate. Toluene (300 mL) is added to improve phase separation and the organic solution is washed with 2×300 mL of water. Toluene is removed on a rotary evaporator under a water aspirator vacuum. The organic product is then returned to a 1000 mL three neck round bottom flask and residual water is removed under vacuum at 60° C. for 3 hours. The product is filtered through a coarse fritted glass funnel yielding 692.0 g (95.2%) of a clear yellow viscous liquid with the following physical and chemical properties:

| | |
|---|---|
| Nitrogen Content | 3.00 wt % |
| Sulfur Content | 19.28 wt % |
| Viscosity @ 40° C. | 116 cSt |
| Low Molecular Weight GPC Analysis | 91.3% dialkylated product (r.t. = 22.6 min) |
| TGA Weight Loss | 10% loss @ 236° C. |
| | 25% loss @ 269° C. |
| | 50% loss @ 288° C. |

FT-IR, $^{13}$C-NMR and H-NMR analysis confirms that the main component of the mixture is the 2-ethylhexyl 3-[[3-[[dibutylamino]thioxomethyl]thio]-2-hydroxypropyl]thio] propanoate having the following chemical structure:

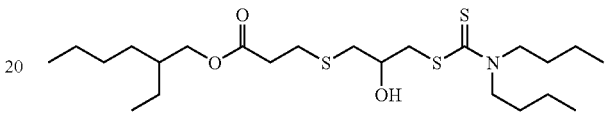

Example 11

A 1000 mL four neck round bottom flask is equipped with a mechanical stirrer, an addition funnel, a thermometer, and a reflux condenser cooled to approximately 5° C. Dry nitrogen is passed into the reactor through the addition funnel and out of the reactor through the reflux condenser. The reactor is chilled with an ice water bath and charged with epichlorohydrin (46.3 g, 0.50 mol) and n-dodecylmercaptan (101.2 g, 0.50 mol). The mixture is stirred with cooling to approximately 5–10° C. Sodium hydroxide (21.0 g, 0.52 mol), water (240 g) and tetrabutylammonium hydroxide (40% in water, 7.0 g, 7 mmol) are combined with mixing and slowly added to the epichlorohydrin and n-dodecylmercaptan over a 1 hour period. An exotherm is observed and cooling is continued maintaining the reaction temperature between 5–10° C. during the addition. After the addition the reaction is heated for 2 hours at 50° C. and cooled to 5° C. Carbon disulfide (40.0 g, 0.53 mol) is then added rapidly to the reaction mixture. Next, dibutylamine (64.6 g, 0.50 mol) is slowly added over 1 hour while maintaining the reaction temperature between 5–15° C. After the addition the reaction is heated at 80° C. for 1 hour and then 1.0 g of 30% hydrogen peroxide is added at 80° C. The reaction is heated at 80° C. for an additional 30 minutes, cooled to 50° C., and the phases separated. The organic portion is washed with 2×100 ML of water. The organic solution is returned to a 500 mL three neck round bottom flask and residual water is removed under vacuum at 60° C. for 2 hours. The product is filtered through a coarse fritted glass funnel yielding 226.6 g (97.7%) of a clear yellow viscous liquid with the following physical and chemical properties:

| | |
|---|---|
| Nitrogen Content | 3.10 wt % |
| Sulfur Content | 19.21 wt % |
| Viscosity @ 40° C. | 85 cSt |
| Low Molecular Weight GPC Analysis | 96.8% dialkylated product (r.t. = 22.3 min) |
| TGA Weight Loss | 10% loss @ 228° C. |
| | 25% loss @ 267° C. |
| | 50% loss @ 287° C. |

FT-IR, $^{13}$C-NMR and H-NMR analysis confirms that the main component of the mixture is the 3-(n-dodecylthio)-2-hydroxypropyl dibutyl carbamodithioate having the following chemical structure:

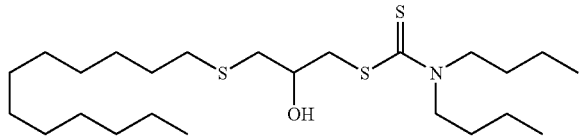

Example 12

A 250 mL four neck round bottom flask is equipped with a mechanical stirrer, an addition funnel, a thermometer, and a reflux condenser cooled to approximately 5° C. Dry nitrogen is passed into the reactor through the addition funnel and out of the reactor through the reflux condenser. The reactor is chilled with an ice water bath and charged with epichlorohydrin (11.6 g, 0.125 mol) and tert-dodecylmercaptan (25.3 g, 0.125 mol). The mixture is stirred with cooling to approximately 5–10° C. Sodium hydroxide (5.2 g, 0.13 mol), water (60 mL) and tetrabutylammonium hydroxide (40% in water, 1.75 g, 1.7 mmol) are combined with mixing and slowly added to the epichlorohydrin and tert-dodecylmercaptan over a 1 hour period. An exotherm is observed and cooling is continued maintaining the reaction temperature between 5–10° C. during the addition. After the addition the reaction mixture is slowly warmed to room temperature over 1½ hours. The reaction is heated for an additional 1 hour at 50° C. and then cooled to 5° C. Carbon disulfide (10.0 g, 0.131 mol) is added rapidly to the reaction mixture. Then bis(2-ethylhexyl)amine (30.3 g, 0.125 mol) is slowly added over 1 hour while maintaining the reaction temperature between 5–15° C. The reaction is heated at 80° C. for 1 hour and diluted with 60 mL of toluene. The phases are separated and the organic portion is washed with 50 mL of water. The organic solution is dried with MgSO$_4$ and concentrated on a rotary evaporator for 2 hours. A yellow viscous liquid (69.9 g, 96.7%) is isolated. Sulfur content=15.26 wt %, Nitrogen content=2.66 wt %. Low molecular weight GPC analysis of the liquid shows the presence of a main peak (90.7%, r. t.=22.1 min) corresponding to a product formed by dialkylating epichlorohydrin. FT-IR, $^{13}$C-NMR and H-NMR analysis confirms that the main component of the mixture is the 3-(tert-dodecylthio)-2-hydroxypropyl bis(2-ethylhexyl)carbamodithioate having the following chemical structure:

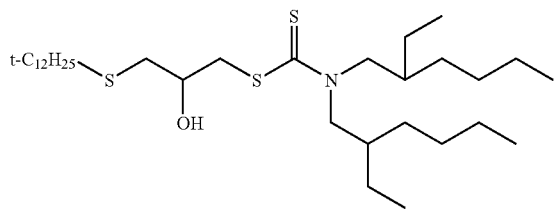

Example 13

In a procedure analogous to that followed in example 12, 2-ethylhexylamine is reacted with tert-dodecylmercaptan, epichlorohydrin, and carbon disulfide. A yellow viscous liquid (56.2 g, 96.6%) is isolated. Sulfur content=19.43 wt %, Nitrogen content=3.37 wt %. Low molecular weight GPC analysis of the liquid shows the presence of a main peak (79.9%, r. t.=22.5 min) corresponding to a product formed by dialkylating epichlorohydrin. FT-IR, $^{13}$C-NMR and H-NMR analysis confirms that the main component of the mixture is 3-(tert-dodecylthio)-2-hydroxypropyl 2-ethylhexylcarbamodithioate having the following chemical structure:

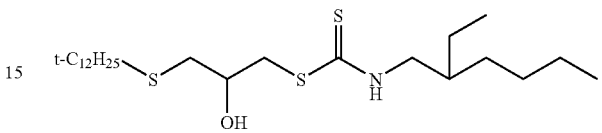

Example 1-M

Preparation of a Sulfur-Free Organo-Molybdenum Compound

Example 14

A variety of hydroxy-substituted dithiocarbamates and sulfur-free organo-molybdenum compounds were blended into an SAE Grade 5W-30 type motor oil as shown in Table 1. These oils contained a typical dispersant inhibitor package and were formulated with a low sulfur and low aromatic hydrocracked and isodewaxed basestock that meets the API Group II category. The oils contained 500 ppm phosphorus derived from secondary zinc dialkyldithiophosphate (ZDDP), HiTEC® 7169, available from Ethyl Corporation. Molyvan® 855, a sulfur-free organo-molybdenum compound derived from an organic amide, was obtained from the R. T. Vanderbilt Company. For comparison, a commercial sulfurized olefin antioxidant (SO), HiTEC® 7084, available from Ethyl Corporation, was included in the study. All additive treat rates for the dithiocarbamates and sulfurized olefin were based on delivering equal sulfur to the finished motor oil (750 ppm, 1500 ppm, and 2250 ppm sulfur respectively as indicated in Table 1). Therefore, the higher the sulfur content of the additive, the lower the additive treat rate to the finished oil. It is desirable to have low additive treat rates. The antiwear properties of the blended motor oils were determined using the Four Ball Wear Test as defined in ASTM D-4172. This test is conducted in a device comprising four steel balls, three of which are in contact with each other in one plane in a fixed triangular position immersed in a reservoir containing the test oil. The fourth ball is above and in contact with the other three. In conducting the test, the upper ball is rotated while it is pressed against the other three balls while pressure is applied by weight and lever arms. The diameter of the scar on the three lower balls is measured by means of a low-power microscope, and the average diameter measured in two directions on each of the three lower balls is taken as a measure of the antiwear characteristics of the oil. A larger scar diameter means more wear. The balls were immersed in the blended motor oils that were previously treated with 1.0 wt. % of cumene hydroperoxide being added to promote wear. Applied load was 40 kg and rotation was at 1200 rpm for 60 minutes at 75° C. Test results are reported in Table 1. Oil sample 1 contained 0.6 wt. % HiTEC® 7169 as the only antiwear additive which delivered approximately 500 ppm phosphorus and 1000 ppm sulfur to the finished motor oil. Oil samples 2 and 3 contained 0.6 wt. % HITEC® 7169 and 0.40 wt. % of molybdenum containing additives that delivered approximately 320 ppm molybdenum to the finished motor oil. Oil samples 4, 5, 6, 13, 14, 15, 22, 23, 24, 31, 32, 33, 40, 41, and 42 contained 0.6 wt. % HiTEC® 7169 and the hydroxy-substituted dithiocarbamates or sulfurized olefins. Oil samples 7, 8, 9, 10, 11, 12, 16, 17, 18, 19, 20, 21, 25, 26, 27, 28, 29, 30, 43, 44, and 45 contained 0.6 wt. % HiTEC® 7169, 0.40 wt. % of the molybdenum containing additives, and the hydroxy-substituted dithiocarbamates or sulfurized olefins.

The results in Table 1 show that the best wear control is achieved when the hydroxy-substituted dithiocarbamates of the present invention are used in combination with the organo-molybdenum compounds and the secondary zinc dialkyldithiophosphate (ZDDP). Table 1 also shows that the sulfurized olefin is not an effective wear inhibitor when used in combination with the organo-molybdenum compounds and the secondary zinc dialkyldithiophosphate (ZDDP).

TABLE I

| Oil Sample | MO wt % | MO Molyvan 855 wt % | Hydroxy Dithio-carbamate Type | Hydroxy Dithio-Carbamate Treat Level wt % (ppm S) | Sulfurized Olefin HITEC 7084 wt % | Four-Ball Wear Scar (mm) | Improvement Over Oil 1 (>/= 0.05 wear reduction) | Improvement Over Oil 2 (>/= 0.05 wear reduction) | Improvement Over Oil 3 (>/= 0.05 wear reduction) |
|---|---|---|---|---|---|---|---|---|---|
| Baseline | 0 | 0 | None | 0 | 0 | 0.69 | | | |
| 1 | 0 | 0 | None | 0 | 0 | 0.63 | | | |
| 2 | 0.40 | 0 | None | 0 | 0 | 0.72 | | | |
| 3 | 0 | 0.40 | None | 0 | 0 | 0.58 | x | | |
| 4 | 0 | 0 | Ex. 9 | 0.37 (750) | 0 | 0.54 | x | | |
| 5 | 0 | 0 | Ex. 9 | 0.73 (1500) | 0 | 0.58 | x | | |
| 6 | 0 | 0 | Ex. 9 | 1.10 (2250) | 0 | 0.62 | | | |
| 7 | 0.40 | 0 | Ex. 9 | 0.37 (750) | 0 | 0.63 | | x | |
| 8 | 0.40 | 0 | Ex. 9 | 0.73 (1500) | 0 | 0.52 | x | x | |
| 9 | 0.40 | 0 | Ex. 9 | 1.10 (2250) | 0 | 0.46 | x | x | |
| 10 | 0 | 0.40 | Ex. 9 | 0.37 (750) | 0 | 0.51 | x | | x |
| 11 | 0 | 0.40 | Ex. 9 | 0.73 (1500) | 0 | 0.44 | x | | x |
| 12 | 0 | 0.40 | Ex. 9 | 1.10 (2250) | 0 | 0.44 | x | | x |
| 13 | 0 | 0 | Ex. 10 | 0.38 (750) | 0 | 0.60 | | | |
| 14 | 0 | 0 | Ex. 10 | 0.77 (1500) | 0 | 0.65 | | | |
| 15 | 0 | 0 | Ex. 10 | 1.15 (2250) | 0 | 0.63 | | | |
| 16 | 0.40 | 0 | Ex. 10 | 0.38 (750) | 0 | 0.51 | x | x | |
| 17 | 0.40 | 0 | Ex. 10 | 0.77 (1500) | 0 | 0.48 | x | x | |
| 18 | 0.40 | 0 | Ex. 10 | 1.15 (2250) | 0 | 0.46 | x | x | |
| 19 | 0 | 0.40 | Ex. 10 | 0.38 (750) | 0 | 0.32 | x | | x |
| 20 | 0 | 0.40 | Ex. 10 | 0.77 (1500) | 0 | 0.33 | x | | x |
| 21 | 0 | 0.40 | Ex. 10 | 1.15 (2250) | 0 | 0.44 | x | | x |
| 22 | 0 | 0 | Ex. 11 | 0.38 (750) | 0 | 0.52 | x | | |
| 23 | 0 | 0 | Ex. 11 | 0.77 (1500) | 0 | 0.66 | | | |
| 24 | 0 | 0 | Ex. 11 | 1.15 (2250) | 0 | 0.60 | | | |
| 25 | 0.40 | 0 | Ex. 11 | 0.38 (750) | 0 | 0.52 | x | x | |
| 26 | 0.40 | 0 | Ex. 11 | 0.77 (1500) | 0 | 0.52 | x | x | |
| 27 | 0.40 | 0 | Ex. 11 | 1.15 (2250) | 0 | 0.47 | x | x | |
| 28 | 0 | 0.40 | Ex. 11 | 0.38 (750) | 0 | 0.47 | x | | x |
| 29 | 0 | 0.40 | Ex. 11 | 0.77 (1500) | 0 | 0.46 | x | | x |
| 30 | 0 | 0.40 | Ex. 11 | 1.15 (2250) | 0 | 0.67 | | | |
| 31 | 0 | 0 | Ex. 2 | 0.45 (750) | 0 | 0.70 | | | |
| 32 | 0 | 0 | Ex. 2 | 0.90 (1500) | 0 | 0.64 | | | |
| 33 | 0 | 0 | Ex. 2 | 1.35 (2250) | 0 | 0.61 | | | |
| 34 | 0.40 | 0 | Ex. 2 | 0.45 (750) | 0 | 0.62 | | x | x |
| 35 | 0.40 | 0 | Ex. 2 | 0.90 (1500) | 0 | 0.55 | x | x | |
| 36 | 0.40 | 0 | Ex. 2 | 1.35 (2250) | 0 | 0.56 | x | x | |
| 37 | 0 | 0.40 | Ex. 2 | 0.45 (750) | 0 | 0.58 | x | | x |
| 38 | 0 | 0.40 | Ex. 2 | 0.90 (1500) | 0 | 0.50 | x | | x |
| 39 | 0 | 0.40 | Ex. 2 | 1.35 (2250) | 0 | 0.51 | x | | x |
| 40 | 0 | 0 | None | 0 | 0.38 | 0.63 | | | |
| 41 | 0 | 0 | None | 0 | 0.75 | 0.65 | | | |
| 42 | 0 | 0 | None | 0 | 1.12 | 0.63 | | | |
| 43 | 0 | 0.40 | None | 0 | 0.38 | 0.72 | | | |
| 44 | 0 | 0.40 | None | 0 | 0.75 | 0.56 | x | | |
| 45 | 0 | 0.40 | None | 0 | 1.12 | 0.56 | x | | |

Baseline contains no ZDDP

Example 15

A variety of hydroxy-substituted dithiocarbamates and a sulfur-free organo-molybdenum compound were blended into an SAE Grade 5W-30 type motor oil as shown in Table 2. These oils contained a typical dispersant inhibitor package and were formulated with a low sulfur and low aromatic hydrocracked and isodewaxed basestock that meets the API Group II category. The oils contained 500 ppm phosphorus derived from secondary zinc dialkyldithiophosphate (ZDDP), HiTEC® 7169, available from Ethyl Corporation. Molyvan® 855, a sulfur-free organo-molybdenum compound derived from an organic amide, was obtained from the R. T. Vanderbilt Company. For comparison, a full ZDDP passenger car engine oil formulation was included in the study. The full ZDDP formulation contained 1000 ppm phosphorus from the ZDDP and a commercial sulfurized olefin antioxidant (SO), HiTEC® 7084, available from Ethyl Corporation. All additive treat rates for the dithiocarbamates were based on delivering equal sulfur to the finished motor oil (750 ppm, 1500 ppm, and 2250 ppm sulfur respectively as indicated in Table 2). Therefore, the higher the sulfur content of the additive, the lower the additive treat rate to the finished oil. It is desirable to have low additive treat rates. The oxidation stability of these oils was measured by pressurized differential scanning calorimetry (PDSC) as described by J. A. Walker and W. Tsang in "Characterization of Lubrication Oils By Differential Scanning Calorimetry", SAE Technical Paper Series, 801383 (Oct. 20–23, 1980). Oil samples were treated with an iron (III) naphthenate catalyst (55 ppm Fe) and 2.0 milligrams were analyzed in an open aluminum hermetic pan. The DSC cell was pressurized with 400 psi air containing 50–55 ppm $NO_2$ oxidation catalyst. The instrument was programmed with the following heating sequence: (1) ramp from room temperature to 120° C. at 20° C./minute, (2) ramp from 120° C. to 150° C. at 10° C./minute, (3) ramp from 150° C. to 250° C. at 2.5° C./minute, (4) iso-track at 250° C. for 1 minute. During the temperature ramping sequence an exothermic release of heat was observed. The exothermic release of heat marks the oxidation reaction. The temperature as which the exothermic release of heat is observed is called the oxidation onset temperature and is a measure of the oxidative stability of the oil (i.e. the higher the oxidation onset temperature the greater the oxidative stability of the oil). All oils are evaluated a minimum of 2 times and the results averaged.

Test results are reported in Table 2. The results show that passenger car motor oils containing ZDDP, molybdenum, and the hydroxy-substituted dithiocarbamates showed superior oxidation stability in the PDSC bench test. In many cases the low phosphorus (500 ppm phosphorus) oils containing the three way combination of ZDDP, molybdenum and hydroxy-substituted dithiocarbamates gave better oxidation protection than the full ZDDP formulation containing sulfurized olefin and no molybdenum (reference oil 1). In many cases the three way system gave comparable oxidation performance to a full ZDDP formulation containing molybdenum and sulfurized olefin in the absence of hydroxy-substituted dithiocarbamates (reference oil 2).

The results in Table 2 show that low phosphorus passenger car engine oils with oxidation stability comparable to or better than full ZDDP formulations can be developed by using a combination of hydroxy-substituted dithiocarbamates, molybdenum, and lower levels of ZDDP.

Preparation of Amine/Amide Reaction Product

A four neck reaction flask is equipped with a stirrer, a thermometer, a reflux condenser cooled to approximately 5° C., and a nitrogen inlet. Dry nitrogen is passed into the reactor through the inlet and out of the reactor through the reflux condenser. The amine (Duomeen® C, 250.0 g) is charged to the flask and heated with mixing to 100° C. Oleic acid (Priolene® 6906, 282.4 g) is slowly added to the amine while maintaining the reaction temperature at 100° C. After the addition the reaction mixture is heated at 160° C. for 4 hours. The aminoamide intermediate is then cooled to 85° C. and prepared for the molybdenum incorporation step.

Preparation of Amine/Amide Molybdenum Complex

A dean-stark trap is placed between the reaction flask and the reflux condenser. The reaction solvent (toluene, 400 mL) is added to the reactor and additional solvent is used to fill the dean-stark trap. The reaction is maintained at 80–85° C. while GMO (HiTEC®-7133, 178.4 g), the molybdenum source (molybdenum trioxide from Climax, 127.0 g), process oil (PO#5, 300.0 g) and water (80 mL) are added. The reaction mixture is stirred vigorously and brought to reflux temperature. Water is removed from the reaction via the dean-stark trap, over a 7 hour period. The resulting solution is cooled to 50–60° C., and filtered through a preweighed pad of celite (20.0 g). The filtrate is concentrated on a rotary evaporator until all the solvent is removed. The weight of the product recovered is 1111 g (99.8% of theory).

| Analysis | |
|---|---|
| Moly Content | 7.85 wt % |
| Nitrogen Content | 2.40 wt % |
| Viscosity @ 40° C. | 731 cSt |
| Viscosity @ 100° C. | 40.5 cSt |
| TBN | 33.4 mg KOH/g |
| IR Carbonyls | 1738 $cm^{-1}$, 1638 $cm^{-1}$ |
| TGA 10% wt loss temperature | 241° C. |
| TGA 25% wt loss temperature | 294° C. |
| TGA 50% wt loss temperature | 345° C. |
| TGA 75% wt loss temperature | 393° C. |

TABLE 2

| Oil Sample | Molybdenum Treat level Molyvan(R) 855 wt % | Hydroxy Dithiocarbamate Type | Hydroxy Dithiocarbamate Treat Level wt % (ppm sulfur) | Total ZDDP In Oil HiTEC(R) 7169 wt % (ppm P) | PDSC Onset Temp. (C.) |
|---|---|---|---|---|---|
| Reference 1 | 0 | None | 0 | 1.20 (1000) | 207.8 |
| Reference 2 | 0.4 | None | 0 | 1.20 (1000) | 220.0 |
| 1 | 0 | None | 0 | 0.6 (500) | 199.1 |
| 3 | 0.40 | None | 0 | 0.6 (500) | 211.7 |
| 4 | 0 | Example 9 | 0.37 (750) | 0.6 (500) | 200.1 |

TABLE 2-continued

| Oil Sample | Molybdenum Treat level Molyvan(R) 855 wt % | Hydroxy Dithiocarbamate Type | Hydroxy Dithiocarbamate Treat Level wt % (ppm sulfur) | Total ZDDP In Oil HiTEC(R) 7169 wt % (ppm P) | PDSC Onset Temp. (C.) |
|---|---|---|---|---|---|
| 5  | 0    | Example 9  | 0.73 (1500) | 0.6 (500) | 199.3 |
| 6  | 0    | Example 9  | 1.10 (2250) | 0.6 (500) | 201.6 |
| 10 | 0.40 | Example 9  | 0.37 (750)  | 0.6 (500) | 215.2 |
| 11 | 0.40 | Example 9  | 0.73 (1500) | 0.6 (500) | 217.5 |
| 12 | 0.40 | Example 9  | 1.10 (2250) | 0.6 (500) | 219.2 |
| 13 | 0    | Example 10 | 0.38 (750)  | 0.6 (500) | 200.1 |
| 14 | 0    | Example 10 | 0.77 (1500) | 0.6 (500) | 197.7 |
| 15 | 0    | Example 10 | 1.15 (2250) | 0.6 (500) | 200.4 |
| 19 | 0.40 | Example 10 | 0.38 (750)  | 0.6 (500) | 215.4 |
| 20 | 0.40 | Example 10 | 0.77 (1500) | 0.6 (500) | 220.8 |
| 21 | 0.40 | Example 10 | 1.15 (2250) | 0.6 (500) | 222.6 |
| 22 | 0    | Example 11 | 0.38 (750)  | 0.6 (500) | 200.9 |
| 23 | 0    | Example 11 | 0.77 (1500) | 0.6 (500) | 201.9 |
| 24 | 0    | Example 11 | 1.15 (2250) | 0.6 (500) | 201.4 |
| 28 | 0.40 | Example 11 | 0.38 (750)  | 0.6 (500) | 220.8 |
| 29 | 0.40 | Example 11 | 0.77 (1500) | 0.6 (500) | 220.8 |
| 30 | 0.40 | Example 11 | 1.15 (2250) | 0.6 (500) | 224.6 |
| 31 | 0    | Example 2  | 0.45 (750)  | 0.6 (500) | 196.9 |
| 32 | 0    | Example 2  | 0.90 (1500) | 0.6 (500) | 197.3 |
| 33 | 0    | Example 2  | 1.35 (2250) | 0.6 (500) | 193.8 |
| 37 | 0.40 | Example 2  | 0.45 (750)  | 0.6 (500) | 217.3 |
| 38 | 0.40 | Example 2  | 0.90 (1500) | 0.6 (500) | 217.2 |
| 39 | 0.40 | Example 2  | 1.35 (2250) | 0.6 (500) | 219.0 |

Reference Oils Also Contain 0.6 wt. % sulfurized olefin HiTEC ® 7084

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims. This invention is susceptible to considerable variation in its practice. Accordingly, this invention is not limited to the specific exemplifications set forth hereinabove. Rather, this invention is within the spirit and scope of the appended claims, including the equivalents thereof available as a matter of law. The patentee does not intend to dedicate any disclosed embodiments to the public, and to the extent any disclosed modifications or alterations may not literally fall within the scope of the claims, they are considered to be part of the invention under the doctrine of equivalents.

What is claimed is:

1. An oil-based lubricant composition comprising a molybdenum source; a hydroxy-substituted dithiocarbamate having the formula:

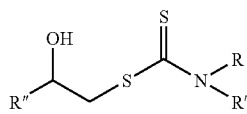

wherein R and R' may be independently hydrogen or alkyl with the requirement that at least one of R or R' is $C_8$ to $C_{22}$ alkyl, R" is R'''XCH$_2$, R'''O(C=O)CH$_2$XCH$_2$, or R'''O(C=O)CH$_2$CH$_2$XCH$_2$ where R''' is $C_1$ to $C_{22}$ alkyl, and X is sulfur (S) or oxygen (O); and optionally, a phosphorous source.

2. The composition of claim 1, wherein R and R' are alkyl.

3. The composition of claim 1, wherein R" is R'''XCH$_2$.

4. The composition of claim 1, wherein R" is R'''O(C=O)CH$_2$XCH$_2$.

5. The composition of claim 1, wherein R" is R'''O(C=O)CH$_2$CH$_2$XCH$_2$.

6. The composition of claim 3, wherein X is oxygen (O).

7. The composition of claim 3, wherein X is sulfur (S).

8. The composition of claim 4, wherein X is oxygen (O).

9. The composition of claim 4, wherein X is sulfur (S).

10. The composition of claim 5, wherein X is oxygen (O).

11. The composition of claim 5, wherein X is sulfur (S).

12. The composition of claim 1, wherein the molybdenum source is selected from the group consisting of molybdenum carboxylates, molybdenum complexes of organic amides, molybdenum complexes of organic amines, and molybdenum dialkyldithiocarbamates.

13. The composition of claim 1, wherein the molybdenum source comprises a molybdenum carboxylate.

14. The composition of claim 1, wherein the molybdenum source comprises a molybdenum complex of an organic amide.

15. The composition of claim 1, wherein the molybdenum source comprises a molybdenum dialkyldithiocarbamate.

16. The composition of claim 1, wherein the phosphorous source is present.

17. The composition of claim 16, wherein the phosphorous source is selected from zinc dialkyldithiophosphates, alkyl phosphites, aryl phosphites, mixed alkyl/aryl phosphites, alkyl thiophosphites, aryl thiophosphites, mixed alkyl/aryl thiophosphites alkyl phosphates, aryl phosphates, mixed alkyl/aryl phosphates, metal or amine salts of phosphorodithioic acids, ashless dialkyldithiophosphates, ashless diaryldithiophosphates, and mixed ashless alkyl/aryldithiophosphates.

18. The composition of claim 16, wherein the phosphorous source comprises zinc dialkyldithiophosphate.

19. The composition of claim 16, wherein the phosphorous source comprises zinc diethyl/diisopropyldithiophosphate.

20. The composition of claim 16, wherein the hydroxy-substituted dithiocarbamate is present in an amount of from about 0.05 to about 1.5 weight percent, the molybdenum source is present in an amount to deliver from about 25 to about 1500 ppm molybdenum, and the phosphorus source is present in an amount to deliver from about 250 to about 1000 ppm phosphorus.

21. A lubricating oil comprising a major amount of a base oil of lubricating viscosity, and a minor amount of a composition of claim 1.

22. The lubricating oil of claim 21, wherein the composition is present in an amount of from about 0.25 to about 2.5 percent by weight of the lubricating oil.

23. The composition of claim 1, wherein the hydroxy-substituted dithiocarbamate is present in an amount of from about 0.05 to about 1.5 weight percent, and the molybdenum source is present in an amount to deliver from about 25 to about 1500 ppm molybdenum.

24. The lubricating oil of claim 21, wherein the base oil of lubricating viscosity is selected from animal oils, vegetable oils, mineral lubricating oils, solvent or acid treated mineral oils, oils derived from coal or shale, hydrocarbon oils, halo-substituted hydrocarbon oils, alkylene oxide polymers, esters of dicarboxylic acids, esters of polyols, esters of phosphorus-containing acids, polymeric tetrahydrofurans, silicon-based oils, and mixtures thereof.

25. The compound 3-(2-ethylhexyloxy)-2-hydroxypropyl bis(2-ethylhexyl) carbamodithioate.

26. A compound with the following chemical formula:

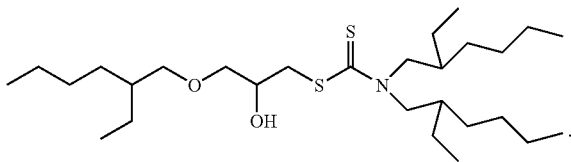

27. A lubricating composition comprising a compound with the following chemical formula:

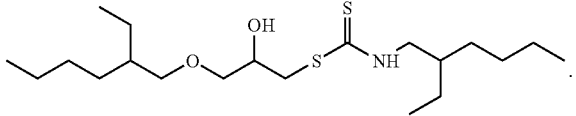

28. The composition of claim 1, wherein the molybdenum source comprises an organo-molybdenum compound.

29. The composition of claim 16, wherein the molybdenum source comprises an organo-molybdenum compound.

30. The composition of claim 16, wherein the molybdenum source comprises an organo-molybdenum compound present in an amount to deliver 25 ppm to 1500 ppm molybdenum, and the hydroxy-substituted dithiocarbamate is present in an amount to deliver 100 ppm to 3000 ppm sulfur, the phosphorus source is present in an amount to deliver about 500 ppm to less than 1000 ppm phosphorus.

31. The composition of claim 16, wherein the molybdenum source comprises an organo-molybdenum compound present in an amount to deliver from 25 ppm to 1500 ppm molybdenum, and the hydroxy-substituted dithiocarbamate is present in an amount to deliver 100 ppm to 2250 ppm sulfur, the phosphorus source is present in an amount to deliver about 500 ppm to less than 1000 ppm phosphorus.

32. The composition of claim 16, wherein the molybdenum source comprises an organo-molybdenum compound present in an amount to deliver from 25 ppm to 1500 ppm molybdenum, and the hydroxy-substituted dithiocarbamate is present in an amount to deliver 100 ppm to 1500 ppm sulfur, the phosphorus source is present in an amount to deliver about 500 ppm to less than 1000 ppm phosphorus.

33. A crankcase oil comprising the composition of claim 16.

34. A composition resulting from contacting a molybdenum source; a hydroxy-substituted dithiocarbamate having the formula:

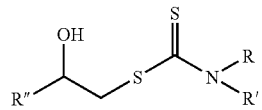

wherein R and R' may be independently hydrogen or alkyl with the requirement that at least one of R or R' is $C_8$ to $C_{22}$ alkyl, R" is R'"$XCH_2$, R'"O(C=O)$CH_2XCH_2$, or R'"O(C=O)$CH_2CH_2XCH_2$ where R'" is $C_1$ to $C_{22}$ alkyl, and X is sulfur (S) or oxygen (O); and a phosphorous source.

35. The composition of claim 34, wherein the molybdenum source comprises an organo-molybdenum compound.

36. The composition according to claim 1, wherein the hydroxy-substituted dithiocarbamate comprises the reaction product produced by combining in substantially equimolar proportions, and in a process carried out in the absence of a reaction solvent: an epoxide, a primary or secondary amine, and carbon disulfide.

37. The composition according to claim 36, wherein the epoxide is selected from the group consisting of methyl glycidyl thioether, ethyl glycidyl thioether, propyl glycidyl thioether, butyl glycidyl thioether, pentyl glycidyl thioether, hexyl glycidyl thioether, cyclohexyl glycidyl thioether, heptyl glycidyl thioether, octyl glycidyl thioether, nonyl glycidyl thioether, decyl glycidyl thioether, undecyl glycidyl thioether, dodecyl glycidyl thioether, tridecyl glycidyl thioether, tetradecyl glycidyl thioether, pentadecyl glycidyl thioether, hexadecyl glycidyl thioether, heptadecyl glycidyl thioether, octadecyl glycidyl thioether, isomers thereof and mixtures thereof.

38. The composition according to claim 36, wherein the epoxide is selected from the group consisting of methyl glycidyl ether, ethyl glycidyl ether, propyl glycidyl ether, butyl glycidyl ether, pentyl glycidyl ether, hexyl glycidyl ether, cyclohexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, heptadecyl glycidyl ether, octadecyl glycidyl ethers, isomers thereof and mixtures thereof.

39. The composition of claim 1, wherein the hydroxy-substituted dithiocarbamate is present in an amount sufficient to deliver from 100 to 1500 ppm sulfur.

40. An oil-based additive concentrate comprising a molybdenum source; a hydroxy-substituted dithiocarbamate having the formula:

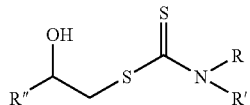

wherein R and R' may be independently hydrogen or alkyl with the requirement that at least one of R or R' is $C_8$ to $C_{22}$ alkyl, R" is R'''XCH$_2$, R'''O(C=O)CH$_2$XCH$_2$, or R'''O(C=O)CH$_2$CH$_2$XCH$_2$ where R''' is $C_1$ to $C_{22}$ alkyl, and X is sulfur (S) or oxygen (O); and, optionally, a phosphorous source.

* * * * *